United States Patent [19]

Clauder et al.

[11] 4,163,851
[45] Aug. 7, 1979

[54] 3α,16α-14,15-DIHYDROEBURNAMENINE

[75] Inventors: Ottó Clauder; Árpád Király; Jozsef Kökösi; Egon Kárpáti; László Szporny, all of Budapest, Hungary

[73] Assignee: Richter Gedeon Vegyészeti Gyár RT, Budapest, Hungary

[21] Appl. No.: 813,227

[22] Filed: Jul. 6, 1977

[30] Foreign Application Priority Data

Jul. 21, 1976 [HU] Hungary .................. RI 592

[51] Int. Cl.$^2$ ......................................... C07D 519/04
[52] U.S. Cl. ..................................... 546/51; 424/256
[58] Field of Search ................... 260/293.53, 293.55; 546/51

[56] References Cited
PUBLICATIONS

Bartlett, M. et al., J.A.C.S., 82, 5941–5946 (1960).
Coffen, D., et al., J.A.C.S., 96, 3966–3973 (1974).
Bartlett, F., et al., Compt. Rend., 249, 1259–1260 (1959).
Chemical Abstracts, 70:29146h (1969) [Blaha, K., et al., Coll. Czech Chem. Comm. 33, 3833 (1968)].
Chemical Absracts, 71:6524m (1969) [Russian Patent 237,339, 2/12/69].
Chemical Abstracts, 58:11413h (1963) [Clauder, O. et al., Tett. Lett., 1962, 1147–1154].
Fieser, L. et al., Advanced Organic Chemistry, Reinhold Pub. Corp., New York, 1961, p. 176.
Houben-Weyl, Methoden der Org. Chemie, 5, 1970, p. 227.
Chemical Abstracts, 63:1764d (1965) [Cervinka, O., et al., Coll. Czech. Chem. Comm., 30, 1700 (1965)].

Primary Examiner—Natalie Trousof
Assistant Examiner—Richard A. Schwartz
Attorney, Agent, or Firm—Karl F. Ross

[57] ABSTRACT

The new compound vincane of the formula

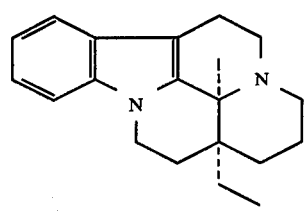

(I)

is prepared by the reduction or reductive dehydratation, respectively, a compound of the formula

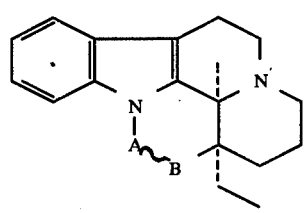

(II)

wherein A∼B represents the group —CH=CH— or

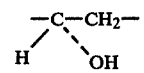

i.e. of vincamenine or of vincanol.

3 Claims, No Drawings

3α,16α-14,15-DIHYDROEBURNAMENINE

The invention relates to a new alkaloid of the vincamine type and the salts thereof.

It has been found that among the decomposition products of the known alkaloid vincamine there are further compounds having valuable physiological activities, not described in the literature hitherto. One of these new therapeutically active compounds is the vincane having the structural formula I

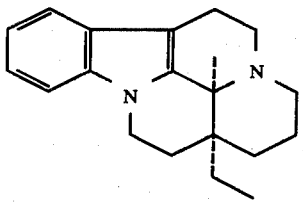

This compound consists of an unsubstituted saturated five-membered ring system, which represents the basic skeleton of the vinca-alkaloids.

According to the present invention, the vincane of the formula I and the salts thereof are prepared by subjecting a compound of the formula II

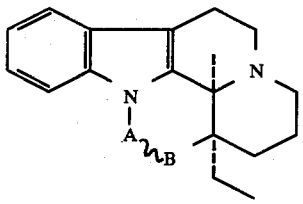

wherein A~B represents either the group (a) or the group (b)

 (a)

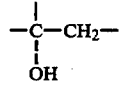 (b)

to reduction or reductive dehydration, respectively, and if desired, converting the obtained product into a salt, and/or liberating the base from the obtained salt thereof, and/or converting it into another salt, preferably into a pharmaceutically acceptable acid-addition salt or quaternary vincanium salt.

The starting materials of the process of the invention can be prepared in the following way:

The compound of the formula II, wherein A~B is the group (a), i.e. the compound vincamenine, can be prepared by dehydration and decarboxylation of vincaminic acid or by decarboxylation of apovincaminic acid, or by dehydration of vincanol.

The compound of the formula II, wherein A~B is the group (b), i.e. the known compound vincanol can be prepared by reducing vincamine with lithium aluminum hydride, as described in the German Pat. No. 1,795,146.

According to the present invention, the reduction of the starting compounds of the formula II can be performed with any reducing agent capable of saturating the double bond which is present originally or is formed by dehydration intermediately between A and B in the compounds of the formula II. Preferably this reduction is performed by the aid of catalytically activated hydrogen or of a chemical reducing agent. In the case of using a compound of the formula II, wherein A~B is the group (a), i.e. vincamenine, as starting material, catalytically activated hydrogen is the more preferred reducing agent, while in the case of using a starting compound of the formula II, wherein A~B is the group (b), i.e. vincanol, the reduction is performed preferably with a chemical reducing agent.

In performing the reduction with catalytically activated hydrogen, a metal catalyst, e.g. palladium, platinum, nickel, iron, copper, cobalt, chromium, zinc, molybdenum or tungsten may be used for this purpose; the most preferred is palladium. Oxides or sulfides of said metals may be used as well. The reduction by catalytic hydrogenation may be performed also in the presence of catalysts precipitated previously onto the surface of a carrier; in this way a substantially smaller amount of the expensive noble metals is needed to accomplish the reduction. Such carriers may be e.g. carbon, especially charcoal, silicon dioxide, alumina, or the sulfates or carbonates of alkaline earth metals. It has been found that especially palladium on charcoal is a preferred catalyst for the reduction with catalytically activated hydrogen according to the present invention. The catalytic hydrogenation can be performed in a solvent inert towards the reaction, e.g. in an aliphatic alcohol. The temperature at which the catalytic hydrogenation of the invention is performed as well as the pressure and the reaction time are of minor importance from the point of view of the performance of the process. It is, however, preferable to carry out the hydrogenation at room temperature and atmospheric pressure and finish the reaction when the calculated amount of one mole of hydrogen is absorbed. The reaction mixture is then processed in known manner, e.g. by filtering off the catalyst after the uptake of hydrogen has ceased and evaporating the solvent from the filtrate. A crystalline substance, the desired vincane is obtained as evaporation residue.

When a chemical reducing agent is used to perform the reduction, preferably formic acid is used for this purpose. As first step of the reduction with formic acid, a dehydration takes place, which is then followed by saturation of the intermediately formed double bond; the intermediate dehydration product, however, is not separated from the reaction mixture and the saturation thereof takes place instantly. The reaction is performed preferably by boiling the compound of the formula II, wherein A~B is the group (b), i.e. the vincanol, in formic acid, preferably in 80% formic acid. The time period of such boiling may be 0.5 to 3 hours. The reaction mixture is then processed in known manner, e.g. in the following way: the major part of the excess of formic acid is evaporated at reduced pressure, the residue is poured into ice water, the pH-value of the mixture is made slightly alkaline by the aid of a dilute aqueous solution of a base, e.g. of sodium hydroxide and then repeatedly extracted with a water-immiscible inert organic solvent, e.g. with a halogenated hydrocarbon, preferably with a chlorinated aliphatic hydrocarbon, e.g. with dichloromethane or chloroform.

The vincane of the formula I is a crystalline compound, which may be purified further, if necessary, by recrystallization. Organic solvents of the ether-type, e.g. diethyl ether, may be used for this purpose.

Various acid-addition salts of vincane can be prepared by reacting the base of the formula I with various acids; these acid-addition salts are mainly crystalline compounds and can be easily identified. Any inorganic or organic acid can be used for this purpose; the most preferred ones are the hydrohalic acid, e.g. hydrochloric acid. As solvents, preferably an aliphatic alcohol, e.g. methanol, can be used in this salt-forming reaction.

Also quaternary salts of vincane can be prepared in the usual manner. e.g. alkyl halides, preferably an alkyl iodide having 1 to 6 carbon atoms may be used as quaternizing agent. To perform this reaction the vincane can be dissolved in an inert organic solvent, preferably in an aliphatic ketone, e.g. in acetone, and the quaternizing agent is added to this solution. The quaternary salts of vincane are crystalline compounds having well-defined melting points.

The products prepared according to the invention, the novel vincane of the formula I and the salts thereof have valuable therapeutic activity.

The haemodynamic effect of vincane hydrochloride was examined on eight dogs narcotized by i.v. doses of 30 mg./kg. of pentobarbital. The substance was administered intravenously, in doses of 1 mg./kg., and the following parameters were registered: arterial blood pressure (MABP), pulse rate (HR), blood flow in the arteria carotis interna and the resistance of this blood vessel (CBF and CVR, respectively), blood flow in the arteria femoralis and the resistance thereof (FBF and FVR, respectively).

The values of the above parameters were measured before the treatment with the drug and then in the third, fifth, tenth and fifteenth minute after the administration thereof. The average values of eight experiments and the percentage deviations thereof are shown in the following table:

| Minute | 3 | 5 | 10 | 15 |
|---|---|---|---|---|
| MABP | +4.1±3.8 | +2.4±3.0 | ±2.2±4.0 | −0.9±1.0 |
| HR | +0.6±9.3 | −9.2±2.2 | −9.0±1.8 | −11.2±4.2 |
| CBF | +10.1±3.2 | +5.4±2.4 | +8.1±4.2 | +5.7±3.5 |
| CVR | −9.5±2.8 | −0.8±2.6 | −4.6±2.6 | −4.8±3.3 |
| FBF | −8.0±18.3 | +0.9±4.2 | −3.4±3.2 | +2.0±4.0 |
| FVR | +4.4±8.3 | +0.8±4.3 | +4.7±3.6 | +0.9±4.0 |

It can be seen from the above results that the substance decreases slightly the pulse rate and has a marked vasodilatatory effect (5–10%) in the cerebral blood vessel.

The effective doses of the substances are between 1 and 5 mg./kg. in the case of intravenous or oral administration. The actual doses are to be determined in each case on the basis of the requirements of the patient and of the experiences of the physician, according to the circumstances of the given case. It is to be noted, however, that the dosage ranges mentioned above cannot be considered as limitations of the invention or of the use thereof.

The vincane of the formula I prepared according to the invention and the salts thereof can be used as active principles in the usual pharmaceutical compositions for parenteral or enteral administration. Such pharmaceutical compositions can be prepared in the usual way, by mixing the active substance with the usual inert, non-toxic, solid or liquid pharmaceutical carriers and/or auxiliary materials. e.g. water, gelatine, lactose, starch, pectin, magnesium stearate, stearic acid, talc, vegetable oils, as arachis oil, olive oil and the like, arabic gum, polyethylene glycol, vaseline etc. may be used as carriers. The compositions may be prepared in the usual pharmaceutical forms, e.g. in the form of solid dosage units, as round or angular tablets, dragees, capsules, e.g. hard gelatine capsules, pills, suppositories etc., or in liquid form, as oily or aqueous solutions suspensions, emulsions, syrups, soft gelatine capsules, injectable oily or aqueous solutions or suspensions, etc. The amount of the solid carriers in the said dosage units may vary between wide limits. The said compositions may contain also usual pharmaceutical auxiliary materials, as preservatives, stabilizers, flavouring substances etc. Also further therapeutically valuable compounds may be added to the said compositions. The form of the dosage units can be selected in accordance with the intended way of administration.

The preparation method of the said pharmaceutical compositions includes the usual technological steps, as grinding, sieving and mixing of the ingredients, granulating, pressing or dissolving. The products may be subjected also to common usual pharmaceutical operations, e.g. to sterilization.

The other therapeutically valuable known compounds, which may be included optionally in the pharmaceutical compositions, are e.g. the following ones: theophylline, phenyl barbiturate, aspirin, vitamines, such as as vitamine E, vitamin P, which may exert a remarkable synergistic effect, vitamine C, i.e. ascorbic acid and the salts and complexes thereof, which promote resorption e.g. in the case of oral administration and accelerate the effect of active substance. The pharmaceutical compositions of the invention may contain the active compound also in the form of the pamoate salt, exerting a prolonged action, or in the form of the dioctyl sulfonate or lauryl sulfate salt; the use of the latter in compositions for oral administration eliminates the bitter taste of the product. The compositions may contain further inorganic salts, such as monoammonium phosphate or monoalkali phosphates, which promote the formation of stable solutions in the compositions for oral administration. The active compound of the invention may be used also in the form of an alkylsulfonate or 2-ketoglutarate salt in the pharmaceutical compositions Further details of the process of the invention are shown by the following examples; it is to be noted, however, that the invention is by no means restricted to the contents of these examples.

EXAMPLE 1

2.78 g. (0.1 mole) of vincamenine are dissolved in 20 ml. of abs. ethanol and the solution is added to a prehydrogenated catalyst containing 1.0 g. of 5% palladium on charcoal in 20 ml. of ethanol. The substance absorbs the calculated amount of hydrogen approximately within five hours and the reaction, i.e. the uptake of hydrogen comes to a standstill. The progress of the hydrogenation may be registered on a saturation curve. After the end of the reaction the catalyst is filtered off and washed thoroughly with 3×10 ml. of absolute ethanol. The filtrate is combined with the washings and evaporated to dryness; an oily residue is obtained, which solidifies on standing a refrigerator. This product crystallizes readily from three parts by weight of acetone. 2.8 g. of vincane are obtained (100% of the theoretical yield).

After recrystallization from acetone, the first crop of the product weighs 1.8 g.; further crystalline product can be obtained by a mild partial evaporation of the mother liquors.

The melting point of the product is 75°–76° C.; the specific rotation: $[\alpha]_D^{20} = +2°$ (1%, chloroform).

EXAMPLE 2

1.0 g. of vincane base is dissolved in 5 ml of ether, an ethanolic solution of 0.13 g. of hydrochloric acid is added to the solution and the salt is precipitated by adding 40 ml. of ether. 1.1 g. of vincane hydrochloride are obtained, m.p. 246°–247° C.

Analysis for $C_{19}H_{24}N_2 \cdot HCl$: calculated: C 72.02%, H 7.94%, N 9.83; found: C 72.15%, H 7.98%, N 9.10%.

EXAMPLE 3

1.47 g. (0.005 mole.) of vincanol in 8 g. of 80% formic acid are boiled for one hour. The excess of the acid is then partially evaporated in vacuo, and the residue is poured into ice water. The pH-value of the obtained solution is adjusted with an aqueous N sodium hydroxide solution to 8–9, and this aqueous solution is extracted 4 to 5 times with dichloromethane. The dichloromethane solution is dried over anhydrous sodium sulfate, filtered and the filtrate is evaporated. 1.20 g. of an oily product are obtained. This oil is then dissolved in acetone. On the next day the precipitated crystals are separated by filtration, washed with a few ml. of ether and dried.

0.60 g. of crystalline vincane are obtained; the recrystallized product melts at 72°–74° C.

EXAMPLE 4

1.50 g. of vincane are dissolved in 15 ml. of acetone and 3 ml. of methyl iodide are added to the solution. The mixture is allowed to stand overnight at room temperature; on the next day the obtained crystals are separated. 2.10 g. of vincanium methyliodide are obtained, m.p. 268°–270° C.

EXAMPLE 5

Tablets containing vincane hydrochloride

The following ingredients are used to prepare the tablets:

| | |
|---|---|
| vincane hydrochloride | 5 mg. |
| gelatine | 3 mg. |
| magnesium stearate | 2 mg. |
| talc | 5 mg. |
| potato starch | 40 mg. |
| lactose | 95 mg. |

The active material is mixed with ¾ part of the potato starch and with the total amount of the lactose. The obtained homogeneous mixture is kneaded together with the aqueous solution of the gelatine and the obtained mass is granulated and dried. The talc, the remained ¼ part of the potato starch and the magnesium stearate are admixed to the granulate and this mixture is pressed into tablets. If desired, the tablets may be provided with dividing scores to facilitate the dosage.

What we claim is:
1. Vincane of the formula:

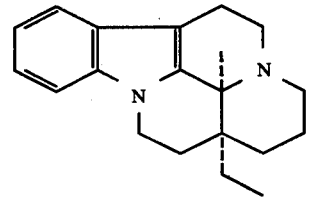

or a pharmaceutically acceptable acid-addition or quaternary salt thereof.
2. Vincane hydrochloride.
3. Vincanium methyliodide.

* * * * *